United States Patent [19]
Raines

[11] Patent Number: 5,973,112
[45] Date of Patent: Oct. 26, 1999

[54] COLLAGEN MIMICS

[75] Inventor: Ronald T. Raines, Madison, Wis.

[73] Assignee: Wisconsin Alumni Research Foundation, Madison, Wis.

[21] Appl. No.: 08/918,223

[22] Filed: Aug. 25, 1997

[51] Int. Cl.[6] .......................... A61K 38/06; C07K 17/00
[52] U.S. Cl. ...................... 530/331; 530/329; 530/345; 530/356
[58] Field of Search ................................ 530/331, 329, 530/345, 356

[56] References Cited

PUBLICATIONS

Gottlieb et al. *Biochemistry*, vol. 4, No. 11 pp. 2507–2513, 1965.
Eberhardt et al. *Journal of the American Chemical Society*, vol. 118, No. 49, pp. 12261–12266, 1996.
Panasik, Jr., et al, *International Journal of Peptide & Protein Research*, vol. 44, pp. 262–269, 1994.
Bella, Jordi, et al., "Crystal and Molecular Structure of a Collagen–Like Peptide at 1.9 Å Resolution," *Science*, 266:75–81 (Oct. 7, 1994).

Eberhardt, Eric S., et al., "Inductive Effects on the Energentics of Prolyl Peptide Bond Isomerization: Implications for Collagen Folding and Stability," *Journal of the American Chemical Society*, 118(49):12261–12266 (1996).
Gottlieb, A. Arthur, et al., "Incorporation of cis–and trans–4–Fluoro–L–prolines into Proteins and Hydroxylation of the trans Isomer During Collagen Biosynthesis," *Biochemistry*, 4(11)2507–2513 (Nov. 1965).
Panasik, Nicholas, Jr., et al., "Inductive effects on the structure of proline residues," *International Journal of Peptide & Protein Research*, 44:262–269 (1994).
Sakakibara, Shumpei, et al., "Synthesis of $(Pro–Hyp–Gly)_n$ of defined molecular weights Evidence for the stabilization of collagen triple helix by hydroxypyroline," *Biochimica et Biophysica Acta*, 303:198–202 (1973).

*Primary Examiner*—Cecilia J. Tsang
*Assistant Examiner*—Abdel A. Mohamed
*Attorney, Agent, or Firm*—Quarles & Brady LLP

[57] ABSTRACT

A novel collagen mimic comprising a tripeptide unit having the formula $(XaaFlpGly)_n$, where Flp is 4(R)-fluoro-L-proline, is disclosed. The collagen mimic has increased stability relative to the collagen-related triple helices $(ProProGly)_n$ and $(ProHypGly)_n$.

11 Claims, 3 Drawing Sheets

COLLAGEN MIMICS

STATEMENT REGARDING FEDERALLY SPONSORED RESEARCH OR DEVELOPMENT

This invention was made with government support under grant AR 44276, awarded by the National Institutes of Health, and by an Arthritis Foundation postdoctoral fellowship awarded to Dr. Steven K. Holmgren. The United States Government has certain rights in this invention.

CROSS-REFERENCE TO RELATED APPLICATIONS

Not applicable.

BACKGROUND

Collagen is the most abundant protein in vertebrates, occurring in virtually every tissue, including skin, tendon, bone, blood vessel, cartilage, ligament, and teeth. Collagen serves as the fundamental structural protein for vertebrate tissues. Collagen abnormalities are associated with a wide variety of human diseases, including arthritis, rheumatism, brittle bones, atherosclerosis, cirrhosis, and eye cataracts. Collagen is also critically important in wound healing. Increased understanding of the structure of collagen, and of how its structure affects its stability, facilitates the development of new treatments for collagen-related diseases and improved wound healing treatments.

Collagen is a fibrous protein that can exist in a variety of related forms. Mammals produce at least 17 distinct polypeptide chains that combine to form at least 10 variants of collagen. In each of these variants, the polypeptide chains of collagen are composed of approximately 300 repeats of the sequence X-Y-Gly, where X is often a proline (Pro) residue and Y is often a 4(R)-hydroxyproline (Hyp) residue. In connective tissue (such as bone, tendon, cartilage, ligament, skin, blood vessels, and teeth), individual collagen molecules are wound together in tight triple helices. These helices are organized into fibrils of great tensile strength, Jones & Miller, *J. Mol. Biol.*, 218:209–219 (1991). Varying the arrangements and cross linking of the collagen fibrils enables vertebrates to support stress in one-dimension (tendons), two-dimensions (skin), or three-dimensions (cartilage).

In vertebrates, the collagen polypeptide is translated with the typical repeat motif being ProProGly. Subsequently, in vivo, the hydroxylation of Pro residues is performed enzymatically after collagen biosynthesis but before the chains begin to form a triple helix. Thus, hydroxylation could be important for both collagen folding and collagen stability. The hydroxyl group of Hyp residues has long been known to increase the thermal stability of triple-helical collagen, Berg and Prockop, *Biochem. Biophys. Res. Comm.*, 52:115–120 (1973). For example, the melting temperature of a triple helix of $(ProHypGly)_{10}$ chains is 58° C., while that of a triple helix of $(ProProGly)_{10}$ chains is only 24° C., Sakakibara et al., *Biochem. Biophys. Acta*, 303:198–202 (1973). In addition, the rate at which $(ProHypGly)_{10}$ chains fold into a triple helix is substantially greater than the corresponding rate for $(ProProGly)_{10}$ chains, Chopra and Ananthanarayanan, *Proc. Natl. Acad. Sci. USA*, 79:7180–7184 (1982). The molecular basis for these observed effects is, however, not clear.

Molecular modeling based on the structure of triple-helical collagen and conformational energy calculations suggest that hydrogen bonds cannot form between the hydroxyl group of Hyp residues and any main chain groups of any of the collagen molecules in the same triple helix, Okuyama et al., *J. Mol. Biol.*, 152:247–443 (1981). Several models include the hypothesis that hydroxyproline increases the stability of collagen as a result a bridge of water molecules formed between the hydroxyl group and a main chain carbonyl group. For reviews of observations advancing this hypothesis, see: Suzuki et al., *Int. J. Biol. Macromol.*, 2:54–56 (1980), and Némethy, in Collagen, published by CRC press (1988), and the references cited therein.

However, there exists experimental evidence that is inconsistent with the bridging water molecule model. For example, the triple helices of $(ProProGly)_{10}$ and $(ProHypCly)_{10}$ were found to be stable in 1,2-propanediol, and Hyp residues conferred added stability in these anhydrous conditions, Engel et al., *Biopolymers*, 16:601–622 (1977), suggesting that water molecules do not play a part in the added stability of $(ProHypcly)_{10}$. In addition, heat capacity measurements are inconsistent with collagen having more than one bound water per six Gly-X-Y units, Hoeve and Kakivaya, *J. Phys. Chem.*, 80:754–749 (1976). Accordingly, there exists no prior definitive demonstration of the mechanism by which the hydroxyproline residues stabilizes collagen triplexes.

A better understanding of how the structure of collagen contributes to its stability would facilitate the design of a collagen or collagen mimics having improved stability. A high stability collagen substitute could advance the development of improved wound healing treatments.

In recent years, there have been exciting developments in wound healing, including the development of tissue engineering and tissue welding. For example, autologous epidermal transplantation for the treatment of burns was a significant advance in tissue engineering. Tissue engineering has also led to the development of several types of artificial skin, some of which employ human collagen as a substrate. However, a major problem associated with this treatment is the fragility of these grafts during and after surgery.

Tissue welding is a wound healing technique in which a laser is used to thermally denature the collagen in the skin at the periphery of a wound. The wound is reannealed by permitting the renaturation of the collagen. In the case of large wounds, a "filler" or solder is required to effect reannealing of the wound. Various materials, including human albumin, have been used as solders for this purpose. A good solder is resilient and is non-immunogenic and should preferably be capable of interaction with native collagen in adjacent sites.

Collagen is also used for a variety of other medical purposes. For example, collagen is used in sutures which can be naturally degraded by the human body and thus do not have to be removed following recovery. A sometimes limiting factor in the design of collagen sutures is the strength of the collagen fibers. A collagen variant or mimic having a greater strength would aid in the usage of such collagen sutures by relieving this limitation.

What is needed in the art is a novel collagen having increased stability for use in artificial skin, as a solder in tissue welding, and as a general tool for use in the design of medical constituents.

Fluoroproline (Flp) was synthesized by Gottleib et al., *Biochemistry*, 4:11:2507–2513 (1965) in both R and S stereoisomers. Gottleib et al. claimed to have incorporated both isomers into collagen by a biosynthetic route, but that claim was later refuted by Takeuchi et al., *Biochem. Biophys.*

Acta, 175:156–164 (1969), Takeuchi and Prockop, *Biochem. Biophys. Acta*, 175:142–155 (1969), and Uitto and Prockop, *Arch. Biochem. Biophys.*, 181:293–299 (1977). Because Gottleib et al. used biosynthesis, to the extent that Flp was incorporated at all into the resulting collagen molecules, it would have been incorporated randomly into the polypeptide in place of some random proline residues. There is, of course, no codon specific for Flp. The Flp was also a racemic mixture of both stereoisomers further randomizing the nature of the proteins produced, if the Flp was incorporated at all, which is significantly in doubt. Others have studied the chemical properties of Flp without incorporating it into a larger polypeptide, Gerig and McLeod, *J. Am. Chem. Soc.*, 98:3970–3975 (1976).

SUMMARY OF THE INVENTION

The present invention is summarized in that a novel variant of collagen has been designed which forms a stronger triple helix than does native collagen. The novel variant includes a fluorinated proline residue substituted for the hydroxyproline residue characteristic of the triple repeats normally found in native collagen.

It is an object of the present invention to provide a novel, high stability collagen molecule that could be used as a component in artificial skin, as a solder in tissue welding, or as a substitute for collagen in other applications requiring high strength.

It is a feature of the present invention that evidence is provided to demonstrate the nature of the additional stability added to collagen by the Hyp residue, thereby making it possible to design other residues for that position which would add to that stability.

The present invention features a novel collagen mimic having increased strength and describes alternative methods by which that molecule can be made.

Other objects, advantages, and features of the present invention will become apparent upon review of the specification, drawings, and claims.

DETAILED DESCRIPTION OF THE INVENTION

Figure 1:
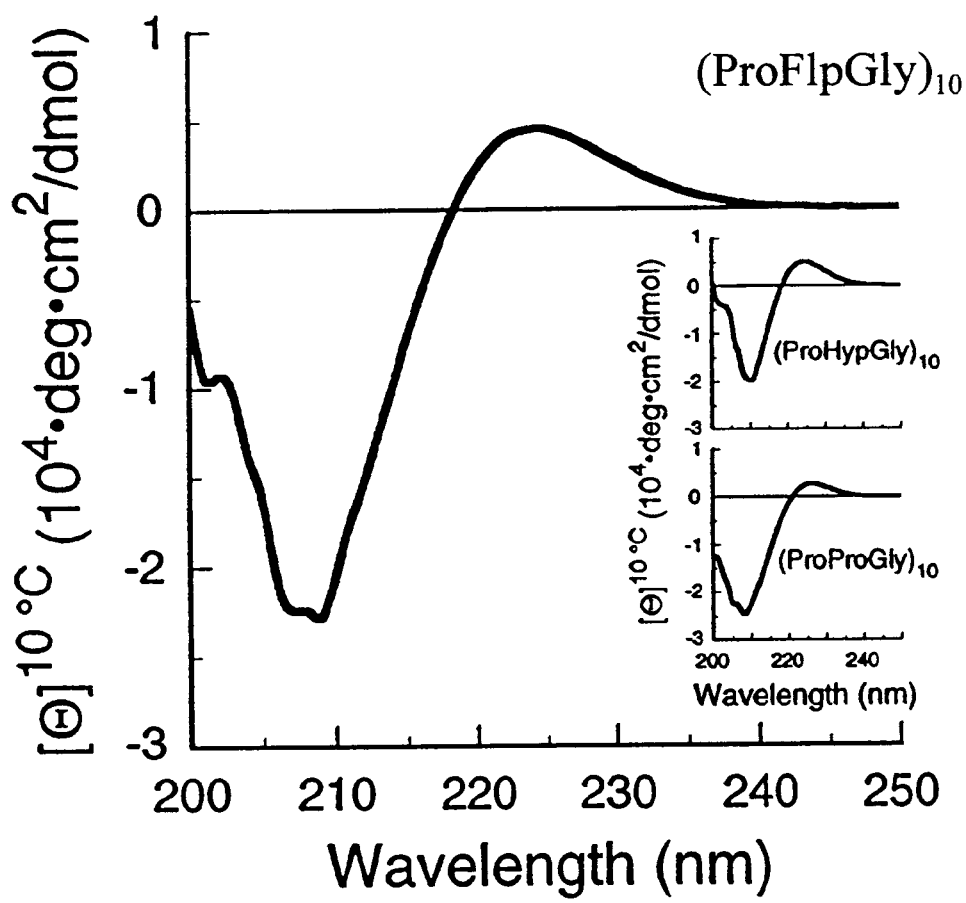
FIG. 1 shows the circular dichroism spectra of (Pro-Flp-Gly)$_{10}$, (ProProGly)$_{10}$, and (ProHypGly)$_{10}$.

The investigation that lead to the work described here began with the notion that a better understanding of the factors that contribute to the three dimensional structure and stability of collagen would facilitate the design of a collagen variant having improved strength for use in wound healing, and the development of treatments for people suffering from collagen-related illnesses. It would also provide a general purpose stronger collagen for a variety of purposes.

The hypothesis underlying this study was the belief that bridging water molecules are unlikely to contribute significantly to collagen stability. First, immobilizing one or more water molecules for each Hyp residue would evoke an enormous entropic cost. A water molecule can form 4 hydrogen bonds. In bulk aqueous solution, these 4 hydrogen bonds are formed with other water molecules that are themselves mobile. In contrast, the bridging water molecules of collagen would suffer a far greater loss of entropy because two of their hydrogen bonds would be with collagen, which is immobile relative to a water molecule.

Second, if the bridging water molecules of collagen are indeed important for collagen stability, then it is likely that they would be homogeneous, with one hydrogen-bonding pattern predominating. However, a high-resolution three-dimensional structure of triple-helical collagen suggested that individual Hyp residues bond to 1, 2, 3, or 4 water molecules, forming irregular, complex networks of intrachain or interchain hydrogen bonds, Bella et al., *Science*, 266:75–81 (1994). This heterogeneity and complexity in the hydrogen bonding is inconsistent with the hypothesis that bridging water molecules confer stability to collagen.

Proposed here is an alternative explanation for collagen stability that is based on the influence of inductive effects on collagen conformation and stability. The Hyp residues in crystalline collagen do not have unusual $\Phi$ or $\phi$ bond angles. But, $\overline{\omega}$ angles (which are the dihedral angles of the peptide bond) merit consideration. The trans isomer (that is, the isomer with $\overline{\omega}=180°$) of a proline peptide bond is only slightly favored over the cis isomer (that is, the isomer with $\overline{\omega}=0°$). Yet according to the structure of crystalline collagen, all of the peptide bonds in triple-helical collagen are in the trans conformation. This leads to the hypothesis that Hyp residues could favor the trans conformation.

To begin to test this hypothesis, it was determined how electron-withdrawing groups affect the trans:cis ratio. N-Acetyl proline methylester (AcProOMe), N-acetyl-4(R)-hydroxyproline methylester (AcHypOMe), and N-acetyl-4(R)-fluoroproline (AcFlpOMe) were synthesized and their preferences for the trans state were determined, Eberhardt et al., *J. Am. Chem. Soc.*, 118:12261–12266 (1996). The trans:cis ratio was found to increase in the order: AcProOMe<AcHypOMe<AcFlpOMe (Table 1). Because the trans isomer is the only isomer found in triple helical collagen, this order suggests that the Flp residue will stabilize triple helical collagen more than the Hyp residue, and that the Hyp residue will stabilize triple helical collagen more than the Pro residue.

The origin of this effect on trans:cis ratio was explored by determining the crystalline structures of AcProOMe, AcHypOMe, and AcFlpOMe, Panasik et al., *Int. J. Pept. Protein Res.*, 44:262–269. The C$\gamma$-C$\delta$ bond length was found to decrease in the order: AcProOMe>AcHypOMe>AcFlpOMe (Table 1). This order is consistent with an inductive effect in which the substituent in the 4-position withdraws electron density away from the C$\gamma$-C$\delta$ bond. A shorter C$\gamma$-C$\delta$ bond length diminishes steric clashes between atoms in the trans isomer, but has no effect on the cis isomer. The inductive effect from the hydroxyl group of Hyp residues is consistent with the effect of Hyp on collagen stability. Other manifestations of the inductive effects of Hyp and Flp residues were also found by Panasik et al. and by Eberhardt et al. Similar inductive effects should be manifested in 4(S)-fluoroproline and in 4,4-difluoroproline.

TABLE 1

Inductive effect on the properties of
AcProOMe, AcHypOMe, and AcFlpOMe

| | trans:cis ratio | $\Delta\Delta G$ (kcal/mol) | Cy-C$\delta$ bond length (Å) |
|---|---|---|---|
| AcProOMe | 4.3 | 0 | 1.523 |
| AcHypOMe | 5.8 | 0.18 | 1.510 |
| AcFlpOMe | 6.2 | 0.22 | 1.508 |

This result suggests that if evolution has placed a Hyp residue in the middle position of the triple repeat motif of collagen due to its the inductive effect that draws electron density toward the hydroxyl group of the Hyp residue, then a residue having a substituent which exhibits an even greater inductive effect should be capable of forming a collagen triple helix that is even stronger than native collagen. This invention is based on this premise and the data presented here supports the hypothesis. The placement of the fluorine atom in the 4 position in the proline in 4(R)-fluoroproline (Flp), and the incorporation of Flp into collagen triple helixes, as described below, does in fact increase the strength of the collagen triple helix formation. Thus the intelligent design of improved collagen mimics is enabled for the first time.

To test the role of the inductive effect on collagen stability, the collagen mimic (Xaa-Flp-Gly)$_{10}$ was synthesized, where Flp is 4(R)-fluoro-L-proline, as described in detail in the examples below. In Flp residues, the fluorine atom imposes a strong inductive effect, but does not form hydrogen bonds. The thermal stabilities and helicity of (ProFlpGly)$_{10}$ (ProProGly)$_{10}$, and (ProHypGly)$_{10}$ were determined using circular dichroism. The collagen mimic (ProFlpGly)$_{10}$ was found to form a very stable triple helical collagen, stronger than either of the other forms tested. This demonstrates not only that the collagen mimic (ProFlpGly)$_{10}$ is useful as a collagen mimic for making collagen compatible materials, but that the critical parameter in the formation of the collagen triple helix structure is the inductive effect on electron density at the 4 position in the proline in the middle position of the triple repeat motif. Forms of collagen mimics having other amino acids at the first position in the triple motif is contemplated here.

The present invention is a collagen mimic comprising a triple repeat motif peptide having the formula (XaaFlpGly)n, where Flp is 4(R)-fluoro-L-proline, n is a positive integer, and Xaa is any amino acid, but is typically one of the 20 naturally occurring amino acids. In the examples below, the collagen mimics that were synthesized and tested had a proline residue at position Xaa. It is anticipated that amino acids other than proline would be tolerated in the Xaa position, given that natural collagen has a wide variety of amino acids in the Xaa position, although proline would be the prototypical residue at that position. The residues in the Xaa position can be the same or can vary in identity along a single molecule.

The examples below describe the chemical synthesis of a collagen having the sequence (XaaFlpGly)n. The present invention is intended to encompass a molecule comprising the sequence, regardless of the mode of synthesis. It is anticipated that one skilled in the art of synthesizing biopolymers could make the peptide by using a modification of the chemical synthesis described below. The molecule can be made by direct synthesis, as described below. It is also contemplated that the molecule can be made by fluorination of the prolines in native collagen, either by enzymatic modifications of the immature collagen form (ProProGly)n or by substitution of the hydroxyl group in Hyp in mature collagen (ProHypGly)n with a fluorine atom.

It is not presently possible to obtain the collagen mimic having the XaaFlpGly tripeptide repeat through biosynthesis. Collagen mimics obtained by chemical modification of natural collagens are within the spirit and scope of the present invention.

The success of the present invention relies on the superior electron-withdrawing ability of fluorine, relative to the hydroxyl group of hydroxyproline. It is therefore expected that a chemical modification that enhances the electron-withdrawing ability of the hydroxyl group (as opposed to replacing the hydroxyl group with a fluorine atom) will enhance collagen stability. It is anticipated that chemical modifications to the hydroxyl group of hydroxyproline that increase its electron-withdrawing ability would result in a collagen mimic with increased stability. Proposed chemical modifications of the hydroxyl group of hydroxyproline are described below.

EXAMPLE

Synthesis of Defined Mimics of Triple-helical Collagen

In brief, (ProFlpGly)$_{10}$ was synthesized by segment condensation on a solid phase. FmocProFlpGlyOH units were assembled by standard solution-phase procedures as described in Bodanszky, *The Practice of Peptide Synthesis 2nd Ed.*, Springer-Verlag (1994), from Flp and commercial reagents. The Flp was made as described in Panasik et al., *Int. J. Pept. Protein Res.*, 44:262–269 (1994) and Eberhardt et al., *J. Am. Chem. Soc.*, 118:12261–12266 (1996). For each strand of a triple helical collagen mimic, ten FmocProFlpGlyOH units were coupled on Z-chlorotrityl resin using an ABI 432A peptide synthesizer. The cleaved peptide was purified by HPLC on a Vydac C-18 reversed-phase column. (ProProGly)$_{10}$ and (ProHypGly)$_{10}$ were from Peptides International. All three 30-mers were judged to be >90% pure by HPLC and mass spectrometry.

In more detail, the collagen mimic was synthesized by a route based on tripeptide units of the form: FmocX-Y-GlyOH, where Fmoc is N$^\alpha$-9-fluorenylmethoxycarbonyl. The placement of a glycine residue at the C-terminus of these units avoided problems caused by racemization (via azlactone formation) during the solid-phase coupling of activated peptide fragments. The tripeptide units were synthesized by using standard solution phase techniques (Bodanszky, 1994). The units were assembled with N$^\alpha$-tert-butyloxycarbonyl (Boc) rather than Fmoc protecting groups because Fmoc cannot withstand Pd/C-catalyzed hydrogenolysis that is necessary to deprotect the glycine residue.

Figure 2:
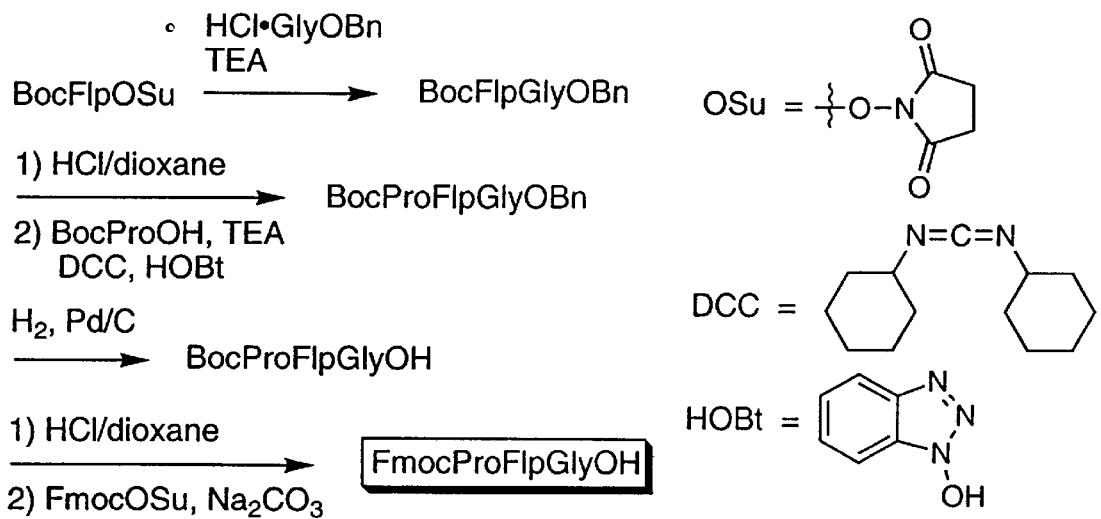
FIG. 2 illustrates the synthetic route for the production of FmocProFlpGlyOH, as described in the examples below.

The synthetic route used to synthesize to FmocProFlpGlyOH (1) is shown in FIG. 2.

Briefly, reaction of BocFlpOSu with GlyOBn yielded a protected dipeptide. Removal of the Boc group in acidic dioxane followed by coupling with BocProOH gives a protected tripeptide. Removal of the benzoyl group by hydrogenolysis yields the Boc analog of 1, which was converted to 1 by removal of the Boc group and reaction with FmocOSu. All reagents used in the synthesis of the tripeptides are available commercially.

TABLE 2

Tripeptide units used in the synthesis of collagen mimic

| | position 1 | position 2 | position 3 |
|---|---|---|---|
| 1 | FmocPro- | Flp- | GlyOH |

A peptide that mimics single strands of collagen was synthesized by solid-phase coupling of tripeptide 1. For a triple helix to be stable at ambient temperature, each strand must contain at least 7 tripeptide repeats. A collagen mimic in which each strand contains 10 tripeptide units was synthesized. This 30-mer was synthesized on 2-chlorotrityl resin, which is amenable to solid-phase synthesis with Fmoc amino acids and allows for the cleavage of the polypeptide from the resin without sidechain or α-amino group deprotection, Fields and Noble, *Int. J. Pept. Protein Res.*, 37:513–520 (1990).

Figure 3:
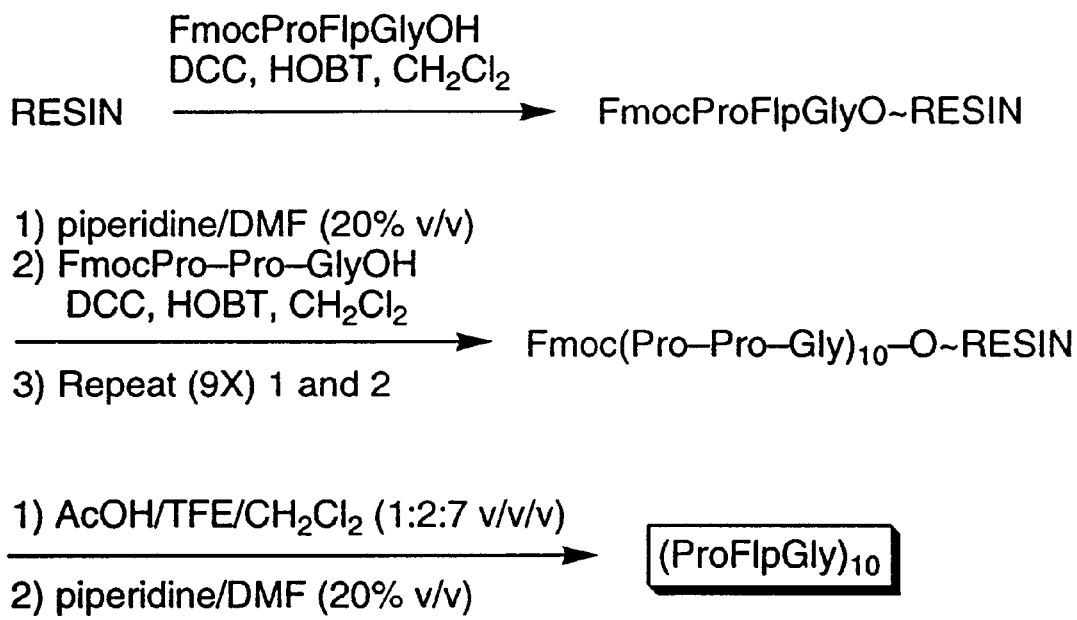
FIG. 3 illustrates the synthetic route for the production of (ProFlpGly)$_{10}$, as described in the examples below.

The route used to synthetic Fmoc(ProFlpGly)$_{10}$-OH is shown in FIG. 3. Briefly, commercial Z-chlorotrityl resin was deprotected with piperidine (Barlos et al., *Int. J. Pept. Protein Res.*, 38:555–562 (1991)) and coupled with FmocProFlpGylOH using DCC and hydroxybenzotriazole (HOBt) to give a resin-bound tripeptide. The deprotection and coupling steps were repeated with tripeptide units until 9 additional units were added. The resulting 30-mer unit was deprotected to give 2 as a free acid (Table 3). 30-Mer peptides 3 and 4 were from Peptides International.

TABLE 3

30-Mer peptides that mimic strands of collagen. Triple helices composed of units 2, 3, or 4 were used for thermodynamic measurements of collagen stability

| 2 | H$_2$N(ProFlpGly)$_{10}$OH |
|---|---|
| 3 | H$_2$N(ProProGly)$_{10}$OH |
| 4 | H$_2$N(ProHypGly)$_{10}$OH |

Stability of Triple Helix

The triple-helical structure of collagen has a characteristic circular dichroism (CD) spectrum, with a peak signal at 225 nm. FIG. 1 shows the CD spectrum of (ProFlpGly)$_{10}$ together with the CD spectra of (ProProGly)$_{10}$ and (ProHypGly)$_{10}$ (inset). Each of the three collagen mimics has a strong signal at 225 nm, which is characteristic of the collagen triple helix.

The melting temperature (T$_m$) of the helix formed by peptides 2–4 was determined by monitoring the CD signal at 225 nm as a function of temperature, according to the method of Long, et al., *Biochemistry*, 32:11688–11695, (1993). Thermal denaturation of the three collagen-related triple helices (80 μM) was performed in 50 mM acetic acid, which is a typical condition for the assessment of collagen stability. The results of this experiment are summarized in Table 4. The (ProFlpGly)$_{10}$ collagen mimic has much greater thermal stability than (ProProGly)$_{10}$ and (ProHypGly)$_{10}$, which is consistent with our hypothesis that the stability of collagen triple helices is related to the inductive effect. Also shown in Table 4 are the free energy changes for each of the three collagen mimics. These values were obtained by the method of Becktel and Schellman, *Biopolymers* 26:1859–1877 (1987).

TABLE 4

Fluoroproline Greatly Stabilizes Triple-Helical Collagen

| Strand | T$_m$(° C.) | ΔΔ G$_m$ (kcal/mol) |
|---|---|---|
| (ProFlpGly)$_{10}$ | 91 | 11 |
| (ProHypGly)$_{10}$ | 69 | 6.5 |
| (ProProGly)$_{10}$ | 41 | 0 |

Each Hyp residue: 6.5 kcal/mol ÷ 30 = 0.2 kcal/mol
Each Flp residue: 11 kcal/mol ÷ 30 = 0.4 kcal/mol These results suggest that the electron-withdrawing ability of the fluorine atom of Flp increases the stability of the collagen triple helix. It is expected that modifying the hydroxyl group of hydroxyproline in collagen so as to increase the electron-withdrawing ability of the hydroxyl group would result in an increase in the stability of the collagen. Ideally, the chemical modification should: (1) make the hydroxyl group more electron withdrawing; (2) be small, so as not to interfere with the packing of triple helices against each other; (3) be uncharged, so as not to interfere with the packing of triple helices against each other. Potentially useful modifications include the addition of an acetyl group, a mesyl (methanesulfonyl) group, or a trifluoromethyl group to the hydroxyl group.

It is speculated that chemical modification of natural collagen to obtain a collagen with increased stability could be obtained as follows. Briefly, natural collagen would be dissolved in an organic solvent. The solvent of choice would likely be polar (to allow the collagen to dissolve) and aprotic (so as not to react with the reagents used in the modification). One solvent having these characteristics is pyridine. It is envisioned that a solution of collagen could be combined with a solution of the chemical modification reagent. If one wished to add an acetyl group, the modification reagent could be acetyl chloride. If one wished to add a mesyl group, the modification reagent could be mesyl chloride. If one wished to add a trifluoromethyl group, the modification reagent could be trifluoromethyl iodide. Each of these reagents could also modify other hydroxyl groups and amino groups on collagen. This may be detrimental to collagen stability. However, it is anticipated that the overall effect would be an increase in stability.

I claim:

1. A collagen mimic comprising a tripeptide having the formula:

(Xaa-Flp-Gly)n, where Xaa is any amino acid residue, Flp is 4(R)-fluoroproline, and n is a positive integer of at least 7.

2. The collagen mimic of claim 1, wherein at least one amino acid residue Xaa is a proline residue.

3. A composition of matter comprising a triple helix of collagen mimic molecules in which each of the molecules in the helix comprises tripeptides of the formula:

(Xaa-Flp-Gly)n, where Xaa is any naturally occurring amino acid,
Flp is 4(R)-fluoroproline, and
n is a positive integer greater than one.

4. A composition of matter as claimed in claim 3 wherein n is at least 7.

5. A composition of matter as claimed in claim 3 wherein Xaa is proline.

6. A collagen mimic comprising a tripeptide having the formula:

(Xaa-Xbb-Gly)n, where Xaa is any amino acid residue,

Xbb is selected from the group consisting of 4(R)-fluoroproline, acetyl modified hydroxyproline, mesly modified hydroxyproline, and trifluoromethyl modified hydroxyproline; and n is a positive integer greater than one.

7. The collagen mimic of claim 6, wherein n is at least 7.

8. The collagen mimic of claim 6, wherein at least one amino acid residue Xaa is a proline residue.

9. The collagen mimic of claim 6, wherein at least one amino acid residue Xaa is a proline residue.

10. A collagen mimic comprising a tripeptide having the formula:

(Xaa-Xbb-Gly)n, where Xaa is any amino acid residue,

Xbb is selected from the group consisting of 4(R)-fluoroproline, 4(S)-fluoroproline, 4,4-difluoroproline, and n is a positive integer greater than one.

11. The collagen mimic of claim 10, wherein n is at least 7.

* * * * *

UNITED STATES PATENT AND TRADEMARK OFFICE
CERTIFICATE OF CORRECTION

PATENT NO. : 5,973,112  Page 1 of 1
DATED : October 26, 1999
INVENTOR(S) : Ronald T. Raines It is certified that error appears in the above-identified patent and that said Letters Patent is hereby corrected as shown below:

Column 1,
Line 6, please delete the entire paragraph and insert the following:

-- This invention was made with government support under grants AR 44276 and GM 44783, awarded by the National Institutes of Health; grants MCB-9057203, BIR-9512577, and BES-9604563 awarded by the National Science Foundation; and by an Arthritis Foundation postdoctoral fellowship awarded to Dr. Steven K. Holmgren. The United States has certain rights in this invention. --

Signed and Sealed this

Twenty-third Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO.        : 5,973,112
APPLICATION NO.   : 08/918223
DATED             : October 26, 1999
INVENTOR(S)       : Ronald T. Raines Page 1 of 1

It is certified that error appears in the above-identified patent and that said Letters Patent is hereby corrected as shown below:

Column 9, Line 5 (claim 6)
     the word "mesly" should be --mesyl--.

Signed and Sealed this

Second Day of October, 2007

JON W. DUDAS
*Director of the United States Patent and Trademark Office*

(12) EX PARTE REEXAMINATION CERTIFICATE (5959th)
United States Patent
Raines

(10) Number: US 5,973,112 C1
(45) Certificate Issued: Oct. 23, 2007

(54) COLLAGEN MIMICS

(75) Inventor: Ronald T. Raines, Madison, WI (US)

(73) Assignee: The National Institutes of Health, Bethesda, MD (US)

Reexamination Request:
No. 90/008,037, May 30, 2006

Reexamination Certificate for:
Patent No.: 5,973,112
Issued: Oct. 26, 1999
Appl. No.: 08/918,223
Filed: Aug. 25, 1997

Certificate of Correction issued Mar. 23, 2004.

(51) Int. Cl.
*A61K 38/06* (2006.01)
*C07K 17/00* (2006.01)

(52) U.S. Cl. .............. 530/331; 530/329; 530/345; 530/356

(58) Field of Classification Search .................. None
See application file for complete search history.

(56) References Cited

PUBLICATIONS

Weber R & Nitschmann H, "Der Einfluss der O–Acetylierung auf das konformative Verhalten des Kollagen–Modellpeptides (L–Pro–L–Hyp–Gly)10 und von Gelatine," Helvetica Chimica Acta 61:701–708 (1978).

*Primary Examiner*—Gary L Kunz

(57) ABSTRACT

A novel collagen mimic comprising a tripeptide unit having the formula $(XaaFlpGly)_n$, where Flp is 4(R)-fluoro-L-proline, is disclosed. The collagen mimic has increased stability relative to the collagen-related triple helices $(ProProGly)_n$ and $(ProHypGly)_n$.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 9 is cancelled.

Claim 6 is determined to be patentable as amended.

Claims 7 and 8, dependent on an amended claim, are determined to be patentable.

New claim 12 is added and determined to be patentable.

Claims 1–5, 10 and 11 were not reexamined.

6. A collagen mimic comprising a tripeptide having the formula:

$$(Xaa\text{-}Xbb\text{-}Gly)_n,$$

where Xaa is any amino acid residue,

Xbb is selected from the group consisting of 4(R)-fluoroproline, [acetyl modified hydroxyproline,] mesyl modified hydroxyproline, and trifluoromethyl modified hydroxyproline; and n is a positive integer greater than one.

*12. The collagen mimic of claim 10, wherein at least one amino acid residue Xaa is a proline residue.*

* * * * *